United States Patent [19]
Olsen

[11] Patent Number: 6,152,898
[45] Date of Patent: Nov. 28, 2000

[54] OVERFILL PROTECTION SYSTEMS FOR IMPLANTABLE DRUG DELIVERY DEVICES

[75] Inventor: James M. Olsen, Plymouth, Minn.

[73] Assignee: Medtronic, Inc., Minneapolis, Minn.

[21] Appl. No.: 09/303,034

[22] Filed: Apr. 30, 1999

[51] Int. Cl.[7] .................................................. A61M 11/00
[52] U.S. Cl. ........................ 604/93.01; 604/132; 604/247
[58] Field of Search ................................ 604/30, 93, 131, 604/132, 246, 247, 141, 151, 156, 133, 153

[56] References Cited

U.S. PATENT DOCUMENTS

| | | | |
|---|---|---|---|
| 3,731,681 | 5/1973 | Blackshear et al. | 604/131 |
| 5,158,547 | 10/1992 | Doan et al. | |
| 5,514,103 | 5/1996 | Srisathapat et al. | 604/141 |
| 5,586,629 | 12/1996 | Shoberg et al. | |
| 5,704,520 | 1/1998 | Gross | 222/334 |
| 5,707,361 | 1/1998 | Slettenmark | 604/131 |
| 5,725,017 | 3/1998 | Elsberry et al. | |

Primary Examiner—Wynn Wood Coggins
Assistant Examiner—Deborah Blyveis
Attorney, Agent, or Firm—Banner & Witcoff, Ltd.

[57] ABSTRACT

A pressure-sensitive overfill protection system for a refillable drug delivery device includes a collapsible link which, in a preferred embodiment, comprises an aneroid having an internal volume of gas at a reference pressure. The collapsible link, in its expanded state, supports on inlet valve in an open position to permit the ingress of new drug fluid into a bellows reservoir. The external surface of the aneroid is exposed to the bellows pressure. When the bellows pressure exceeds the reference pressure, the aneroid collapses and permits the inlet valve to move to a closed position under a biasing force provided by a spring. Further flow of new drug fluid into the drug delivery device is thereby prevented. Moreover, the closure of the valve provides a large increase in pressure is experienced in the refill device and may therefore be sensed by a clinician. Because the overfill protection system is pressure sensitive, it may be used with different sized bellows without modification.

16 Claims, 2 Drawing Sheets

OVERFILL PROTECTION SYSTEMS FOR IMPLANTABLE DRUG DELIVERY DEVICES

BACKGROUND OF THE INVENTION

1. Field of the Invention

The present invention relates generally to implantable drug delivery devices. More particularly, the invention relates to pressure-sensitive overfill protection systems for preventing overfilling and over pressurization of an implantable drug delivery device.

2. Description of Related Art

Implantable drug delivery systems are in widespread use to provide site-specific and/or sustained delivery of beneficial agents to address adverse patient conditions. Such delivery systems may include implantable infusion pumps, which typically include a pressurized drug reservoir and some form of fluid flow control. One example of an implantable infusion pump is the SYNCHROMED™ pump manufactured by Medtronic, Inc. of Minneapolis, Minn.

Typically, implantable drug delivery devices are periodically refilled in situ and percutaneously using a refill device, such as a hypodermic syringe inserted into a refill chamber of the drug delivery device. A common problem related to refilling is the potential for overfilling or over pressurization of the device. Typically, the clinician refilling the device relies upon tactile pressure to sense that the drug reservoir has been filled to capacity. Any additional fluid injected into the device beyond capacity of the reservoir may cause severe damage to the drug delivery device and may cause other adverse consequences.

Prior art overfill prevention devices, such as those described in U.S. Pat. No. 5,158,547, the entire writing of which is incorporated herein by reference, are exemplified by FIG. 1, which is a cross-section of a drug delivery device in the form of an implantable infusion pump 110. Generally, a valve 112 having a rigid valve stem 114 is fastened, usually by welding, to an inner surface 116 of the pump diaphragm or bellows 118. As new drug supply is injected through the septum 120 using a refill device (not shown), the reservoir chamber 122 fills with drug and the surface 116 moves in an expanding direction (downward in FIG. 1). As the reservoir chamber 122 reaches capacity, the valve 112 is pulled into sealing engagement with a valve seat 126, resulting in a detectable increase in pressure in the refill device and preventing overfilling and/or over pressurization of the drug delivery device 110.

Notably, prior art devices are volume-sensitive and rely on the displacement of the bellows surface for actuating an inlet valve. One problem with such devices is that the particular size of the valve stem is dependent on the size of the bellows. Accordingly, when different sized bellows are used in a particular pump configuration, the overfill protection device must be modified to provide for valve closure at the appropriate bellows volume. Another problem with such prior art configurations is that, due to the tolerance stack up, i.e. the overall variation in valve dimensions that results from the dimensions of the various parts that make up the valve, prior art protection systems are typically constructed such that the bellows is slightly underfilled when the valve seats. Thus, the full capacity of the bellows is not utilized.

Another problem with prior art systems is that the over pressurization protection valve stem is welded directly to the bellows surface. In addition to the construction costs associated with this exercise, there is the potential that the bellows, which is typically constructed of a thin metal membrane, may be damaged during the welding or fastening operation.

What is needed is an overfill protection system for implantable drug delivery devices which addresses the aforementioned problems. Specifically, what is needed is an overfill protection system for an implantable drug delivery device that is pressure-sensitive and which is more economical to manufacture than prior art systems.

SUMMARY OF THE INVENTION

The present invention solves the aforementioned problems by providing an overfill protection system for an implantable drug delivery device that incorporates a pressure-sensitive valve for preventing the ingress of fluid when the pressure in the drug delivery device reservoir reaches a predetermined value. Since the valve is pressure-sensitive, it can be used with different sized reservoirs without modification. Moreover, the invention provides a system which eliminates the need to weld or otherwise fasten the valve to the bellows.

In a preferred embodiment, the pressure-sensitive valve is provided on a refill inlet of the drug delivery device. Operably connected to the valve is a pressure-sensitive link, which may be in the form of an aneroid formed by two corrugated diaphragms that define an interior space having trapped fluid therein at a reference pressure. The pressure-sensitive link is characterized by a relatively large displacement for relatively small changes in external pressure. The external surface of the pressure-sensitive link is exposed to the pressure of the drug fluid contained in the drug reservoir.

In operation, as the reservoir is filled with a new drug supply, the pressure on the pressure-sensitive link exterior surface increases. When the reservoir pressure, and therefore the external pressure on the pressure-sensitive link, reaches a predetermined pressure, defined by the reference pressure of the pressure-sensitive link, the aneroid collapses, thereby causing the valve to occlude the inlet passage to the reservoir. Preferably, the valve is spring-biased against an external surface of the aneroid.

The unique advantages provided by the invention permit different sized reservoirs to be used without modification to the overfill protection system. Moreover, since the valve may be spring biased against the actuating surface of the pressure-sensitive link, the invention eliminates the need for welding or otherwise fastening the valve stem of prior art system to the bellows surface and thereby provides for more economical manufacture than prior art systems.

DESCRIPTION OF THE DRAWINGS

These and other advantages and features of the invention will become apparent upon reading the following detailed description and referring to the accompanying drawings in which like numbers refer to like parts throughout and in which.

DETAILED DESCRIPTION OF THE INVENTION

As explained in more detail below, the present invention overcomes the above-noted and other shortcomings of known systems by providing an implantable drug delivery device that includes a pressure-sensitive overfill protection system, which in a preferred embodiment, comprises a pressure-sensitive link in the form of an aneroid containing fluid at a reference pressure. As used herein, the term "fluid" refers to gas, liquid, and/or mixtures of gases and liquids. The pressure-sensitive link is operably connected to the inlet valve of the drug delivery device to prevent the further flow of a refill supply of drug when a predetermined reservoir pressure is attained during a refilling operation.

Figure 1:
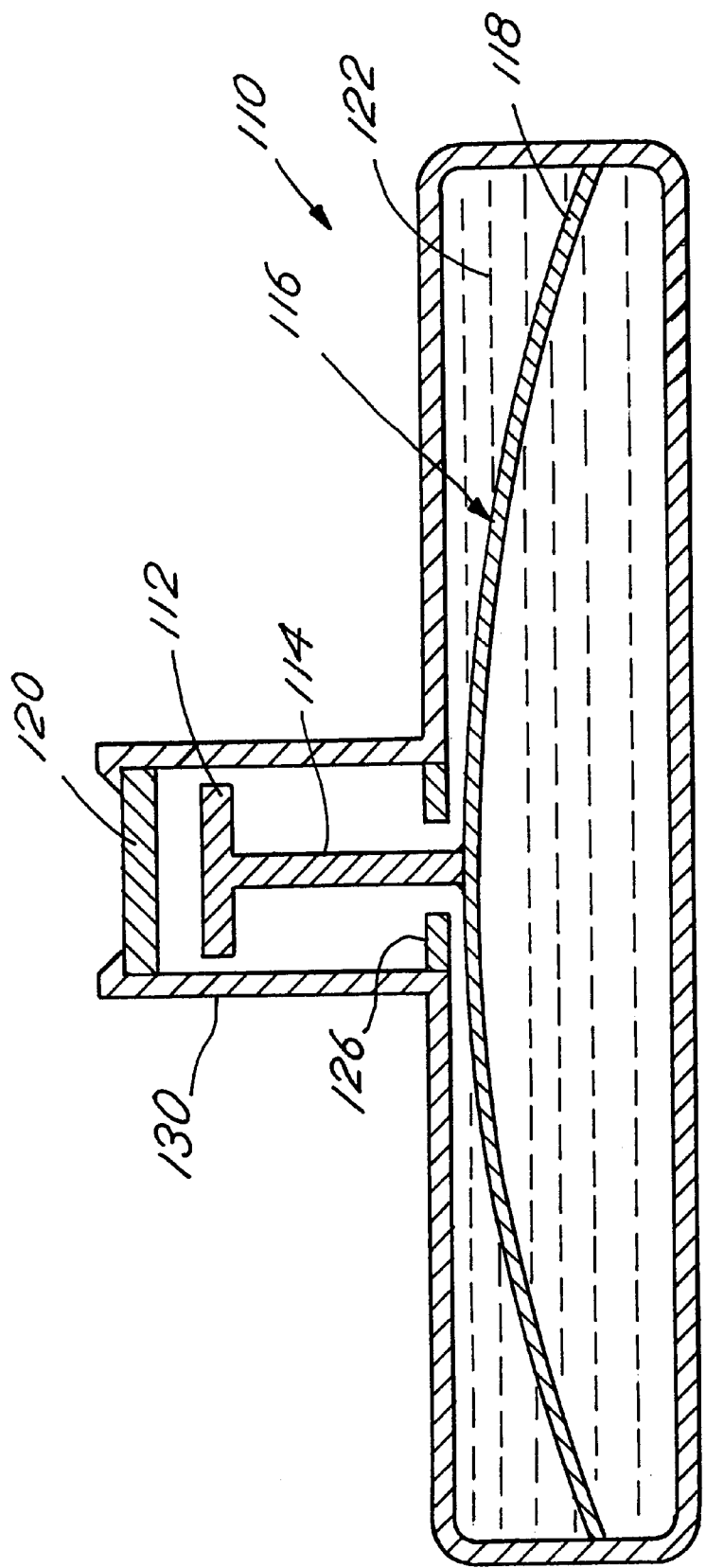
FIG. 1 is cross-section of an overfill protection system according to the prior art as described above.
Figure 2:
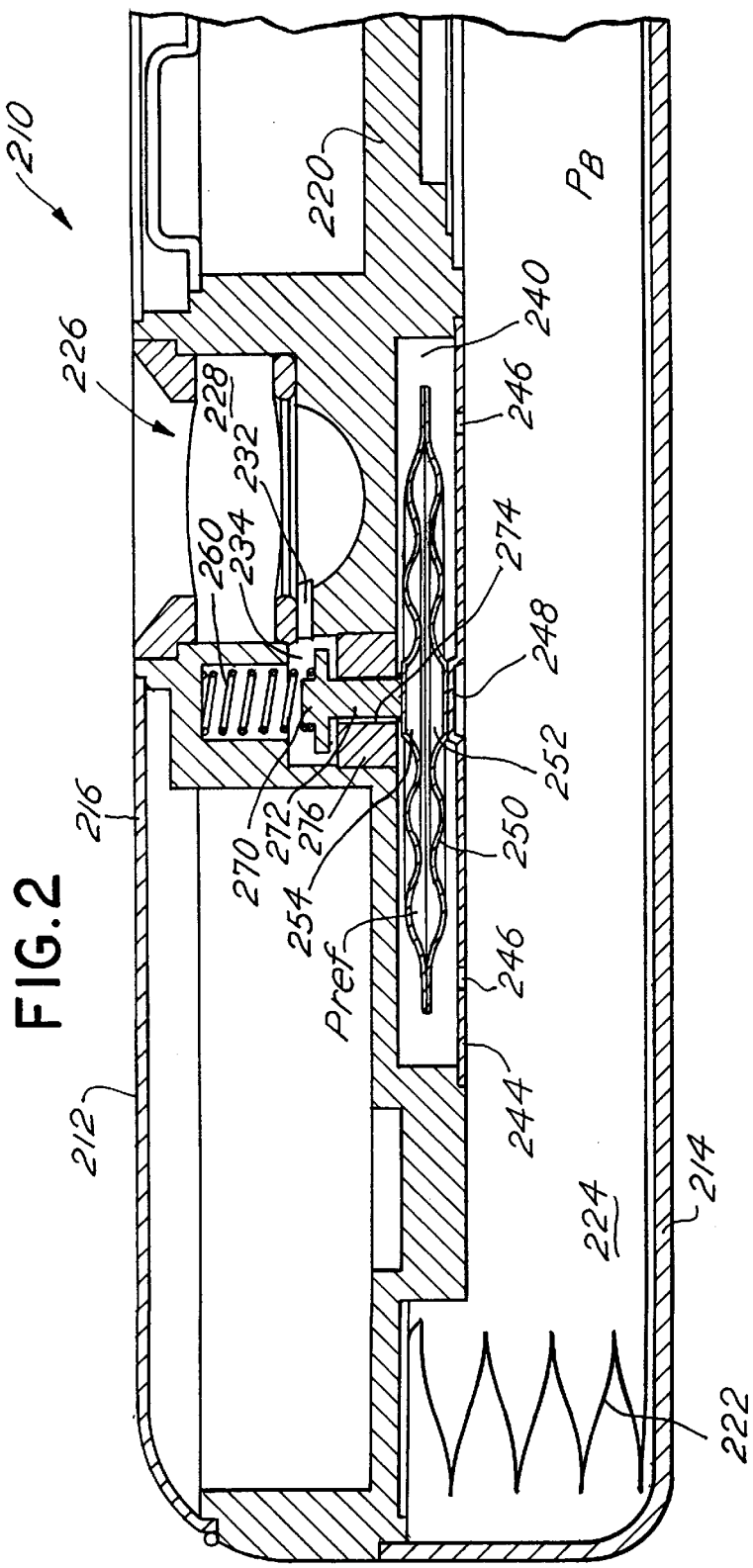
FIG. 2 is a cross-section of an implantable infusion pump incorporating an overfill protection system according to a preferred embodiment of the present invention.

Referring to FIG. 2, a drug delivery device in the form of an implantable infusion pump, generally referenced 210, includes a housing 212 comprised of a back plate 214 and a cover 216 which are attached to a bulkhead 220. A pressure-sensitive drug reservoir 224 is formed by a bellows assembly 222, an open end of which is fastened to the bulkhead 220 in a known manner. Bulkhead 220 also defines a refill port 226 which is provided with a septum 228 for receiving, in a known manner, the needle of a refill device, such as a hypodermic syringe (not shown) for introducing a refill supply of drug into the pump 210.

According to the described embodiment of the invention, the bulkhead 220 is provided with a generally circular recess 240 which houses a pressure-sensitive link 250. A retaining plate 244 maintains the position of the pressure-sensitive link 250 within the bulkhead 220 and is provided with a plurality of ports 246 to permit flow of new drug fluid to the bellows inner chamber 224. The ports 246 permit the outer surface of the pressure-sensitive link to be exposed to the pressure $P_B$ within the bellows inner chamber 224. Retaining plate is provided with a circular support projection 248 which engages a similarly shaped support projection 252 on the lower portion of pressure-sensitive link 250. Similarly, an actuating surface 254 on the upper portion of pressure-sensitive link 250 engages the bottom surface of the cylindrical stem 272 of valve 270. Valve stem 272 is movably disposed in an orifice 274 formed in a valve seat 276 which is mounted within a circular recess in bulkhead 220. A biasing element 260 in the form of a coil spring is provided on the upper surface of the valve to maintain the bottom surface of the valve in contact with the actuating surface 254 of the pressure-sensitive link 250.

In the described embodiment, a valve inlet port 232 provides fluid passage from the refill port 226 to the valve cavity 234. Valve inlet port 232, valve seat orifice 274, recess 240 and retaining plate ports 246 form respective portions of a refill inlet passage 230 which provides for fluid communication between the refill port 226 and the bellows inner chamber 224. Valve seat orifice 274 is dimensioned so as to provide an annular passage around the valve stem 272 to permit the flow of fluid through the valve seat orifice 236 when the valve 270 is in its open position.

Figure 3:
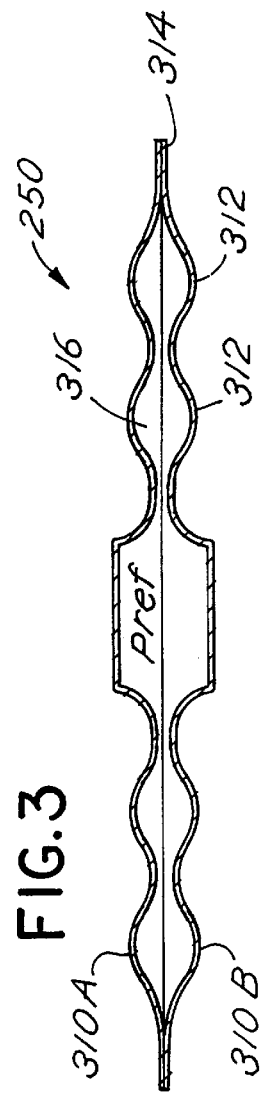
FIG. 3 is detailed view of a pressure-sensitive link according to a preferred embodiment of the present invention.

Referring additionally to FIG. 3, the pressure-sensitive link 250 according to the present invention is comprises of a pair of corrugated diaphragms 310A and 310B, each including a series of corrugations 312 which may be of a constant radius or sinusoidal in shape. Preferably, diaphragms 310 are constructed of titanium sheet metal which is approximately 2 mils in thickness. At their outer peripheries 314, diaphragms 310 are welded or otherwise fastened to each other to define an interior volume 316 occupied by a gas or fluid at a reference pressure $P_{ref}$ when the pressure-sensitive link is in its undeformed state, i.e., subject to no external pressure forces. Preferably, the reference pressure $P_{ref}$ is selected to be substantially equal to the pressure of the fluid in the bellows inner chamber 224 when the bellows is filled to its capacity. As will be recognized by those of ordinary skill, diaphragms 310 may be fastened together in a controlled environment to trap fluid therebetween and to maintain the interior volume of trapped fluid at the reference pressure. It will be understood from the cross-section shown in FIG. 2 that in the illustrated embodiment, pressure-sensitive link 250 is generally circular in shape, although other shapes are contemplated by the invention.

In operation, when the supply of drug in the bellows inner chamber 224 has been depleted, the pressure within the bellows and therefore on the external surface of pressure-sensitive link 250 will be less than the reference pressure $P_{ref}$. Pressure-sensitive link 250 will be in its expanded state (shown in FIG. 2) thereby supporting the valve 270 in an open position against the bias of spring 260. As the implantable pump is refilled using a syringe needle inserted through septum 228, the bellows begins to expand to its filled position. When the capacity of the bellows is reached, the pressure on the external surface of pressure-sensitive link 250 will increase, usually rapidly, and exceed $P_{ref}$. The pressure-sensitive link 250 will eventually collapse, permitting valve 270 to seat against valve seat 276 and preventing further ingress of drug fluid into the bellows inner chamber 224. Closure of valve 270 will prevent overfilling and cause a significant and detectable increase in pressure in the refill syringe so that a technician will signaled to discontinue filling. Pressure-sensitive link 250 thus provides a means for moving the valve 270 to an occluding position in response to a predetermined pressure being attained in the bellows inner chamber 224.

Those of ordinary skill will recognize that the structure of pressure-sensitive link 250 is such that a small pressure differential between the external pressure and $P_{ref}$ results in a relatively large movement or displacement of the opposed surfaces of the pressure-sensitive link. The corrugated structure of the pressure-sensitive link 250 provides for increased inward displacement of the opposed link surfaces in response to pressure differences. Of course, various alternative pressure-sensitive link configurations are intended to be covered by the scope of the appended claims. For example, only a single corrugated surface could be used, or other materials besides titanium metal could be employed in the construction of the pressure-sensitive link.

It will also be recognized that the pressure-sensitive aspects of the invention may be incorporated at various locations within the structure of the implantable pump. Although, the above described embodiment incorporates the pressure sensitive element within the inlet to the bellows reservoir, the pressure sensitive element could be incorporated into the reservoir outlet.

Examples of the more important features of this invention have been broadly outlined above so that the detailed description that follows may be better understood and so that contributions which this invention provides to the art may be better appreciated. There are, of course, additional features of the invention which will be described herein and which will be included within the subject matter of the claims appended hereto. For example, the pressure-sensitive link of the present invention may be constructed using modified forms incorporating more than one internal volume, for example, or incorporating springs or resilient plastics or polymers in their construction or in combination with the disclosed aneroid structure. Moreover, the fluid contained in the pressure-sensitive link may comprise a dual-phase propellant which exists in both gaseous and liquid states so as to provide a constant pressure in a manner similar to known pressurization techniques for the bellows reservoir. The appended claims are intended to cover all such modifications.

What is claimed is:

1. An implantable drug delivery device comprising:
   a) a housing, including a refill port;
   b) a reservoir defining a reservoir chamber and disposed within the housing for storing a supply of fluid;
   c) a refill passage in the housing for conveying fluid from the refill port to the reservoir chamber;
   d) a valve for selectively occluding the refill passage; and
   e) an aneroid connected to the valve, whereby the aneroid moves the valve to an occluding position in response to a predetermined pressure being attained in the reservoir.

2. The device of claim 1, wherein the aneroid is exposed to the pressure within the reservoir.

3. The device of claim 2, wherein the aneroid is comprised of two diaphragms.

4. The device of claim 3, wherein at least one of the diaphragms are corrugated.

5. The device of claim 2, wherein an internal volume of the aneroid is provided with a gas at a reference pressure substantially equal to a desired full reservoir pressure.

6. The device of claim 1, further comprising a biasing element for biasing the valve to the occluding position.

7. The device of claim 6, wherein the biasing element is a coil spring.

8. An implantable drug delivery device comprising:
   a) a housing, including a refill port;
   b) a reservoir disposed within the housing for storing a supply of fluid;
   c) a refill passage in the housing for conveying fluid from the refill port to the reservoir;
   d) a valve for selectively occluding the refill passage; and
   e) a pressure-sensitive link for permitting the valve to move to an occluding position in response to a predetermined pressure being attained in the drug delivery device, the pressure-sensitive link further comprising a pair of opposing diaphragms.

9. The device of claim 8, wherein the pressure-sensitive link is adapted to permit the valve to move in response to a predetermined pressure being attained in the reservoir.

10. The device of claim 8, wherein the pressure-sensitive link is adapted to permit the valve to move in response to a predetermined pressure being attained in an outlet of the delivery device.

11. The device of claim 8, wherein the pressure-sensitive link comprises a collapsible member.

12. The device of claim 11, wherein the collapsible member is an aneroid exposed to the pressure within the reservoir.

13. The device of claim 12, wherein an internal volume of the aneroid is provided with a gas at a reference pressure substantially equal to a desired full reservoir pressure.

14. The device of claim 8, wherein at least one of the diaphragms are corrugated.

15. The device of claim 8, further comprising a biasing element for biasing the valve to the occluding position.

16. The device of claim 15, wherein the biasing element is a coil spring.

* * * * *